United States Patent
Yamauchi

(10) Patent No.: US 8,294,893 B2
(45) Date of Patent: Oct. 23, 2012

(54) FLAME ATOMIC ABSORPTION SPECTROPHOTOMETER

(75) Inventor: Kazuo Yamauchi, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 363 days.

(21) Appl. No.: 12/625,934

(22) Filed: Nov. 25, 2009

(65) Prior Publication Data

US 2010/0134795 A1 Jun. 3, 2010

(30) Foreign Application Priority Data

Nov. 28, 2008 (JP) ................................. 2008-303996

(51) Int. Cl.
*G01J 3/30* (2006.01)
(52) U.S. Cl. ...................................................... 356/315
(58) Field of Classification Search .................. 356/315; 431/22, 77
See application file for complete search history.

(56) References Cited

U.S. PATENT DOCUMENTS

| | | | | |
|---|---|---|---|---|
| 3,583,844 A * | 6/1971 | Smith, Jr. | ...................... | 356/315 |
| 3,711,237 A * | 1/1973 | Jaulmes | ........................... | 431/69 |
| 4,568,267 A * | 2/1986 | Kendall-Tobias | ............... | 431/90 |
| 2002/0045143 A1* | 4/2002 | Kawauchi et al. | ............. | 431/70 |
| 2004/0012779 A1* | 1/2004 | Grey et al. | .................... | 356/315 |

FOREIGN PATENT DOCUMENTS

| | | |
|---|---|---|
| JP | 07-294424 A | 11/1995 |
| JP | 11-183376 A | 7/1999 |
| JP | 2001-013066 A | 1/2001 |
| JP | 2003-035595 A | 2/2003 |
| JP | 2005-069763 A | 3/2005 |
| JP | 2006-167117 A | 6/2006 |
| JP | 3146142 U | 10/2008 |

OTHER PUBLICATIONS

Website of http://www.shimadzu.com/products/lab/spectro/oh80jt0000001kxm.html.
Japanese Office Action dated Aug. 28, 2012, issued in corresponding Japanese Patent Application No. 2008-303996.

* cited by examiner

*Primary Examiner* — Kara E Geisel
(74) *Attorney, Agent, or Firm* — Sughrue Mion, PLLC

(57) ABSTRACT

A flame atomic absorption spectrophotometer in which a combustion gas is burned by a burner to form a flame and a nebulized sample is atomized in the flame, including a flashback detector for detecting an occurrence of a flashback phenomenon of the flame or detecting a state in which a flashback phenomenon is considered to have occurred; a flashback count memory for counting detection of a flashback by the flashback detector and storing a number of count; an ignition inhibitor for inhibiting, in a case where a flashback is detected by the flashback detector, an ignition after the detection; and an inhibition canceller for canceling, in an ignition inhibit state created by the ignition inhibitor, the ignition inhibit state only by a predetermined operation which is changed in accordance with the number of count stored in the flashback count memory.

3 Claims, 5 Drawing Sheets

FLAME ATOMIC ABSORPTION SPECTROPHOTOMETER

The present invention relates to a flame atomic absorption spectrophotometer in which a nebulized sample liquid is introduced to a flame to atomize the sample.

BACKGROUND OF THE INVENTION

In a flame atomic absorption spectrophotometer, a sample liquid which has been nebulized by a spray or in other manner and a combustion gas are mixed in a chamber. The mixed gas is burned while being flowed from a slit opening of a burner head to form a flame. In the flame, components (or elements) of the sample are atomized. When light is cast to the gaseous atoms, only the light of a predetermined wavelength in accordance with the species of the atoms is absorbed. By performing a spectroscopic analysis on this absorbed light, the components in the sample are identified and quantified.

As the combustion gas for making a flame, a mixed gas of a fuel gas, such as acetylene ($C_2H_2$), and a supporting gas, such as air or nitrous oxide ($N_2O$), is generally used. Which of air or nitrous oxide is used as the supporting gas is determined in accordance with the element to be analyzed.

When a combustion gas normally burns, its burning rate and the flow rate of the gas flowing out from the burner head are in equilibrium, so that a flame is stably formed slightly above the upper surface of the burner head. However, if the flow rate of gas flowing out from the burner head is decreased for any reason, the balance between the burning rate and the gas flow rate is lost, so that the flame is drawn into the burner head. This phenomenon is called a "flashback," which is a small-scale explosion produced when the combustion zone of the flame enters into the burner head or into the chamber filled with the combustion gas.

The burning rate is determined by the mixture ratio of the fuel gas and the supporting gas and the temperature around the flame. The burning rate becomes largest (or maximum) at the stoichiometric ratio (at which the reaction gases are completely burned). When a flashback occurs, the magnitude of explosion (or energy) of the flashback becomes larger as the mixture ratio of the gases at that point is closer to the stoichiometric ratio. Major causes of flashback include, for example, a decrease in the supply pressure of the fuel gas or supporting gas (or decrease in the pressure of the tank) and an unexpected failure of a supply pipe of the gas.

Since a flame atomic absorption spectrophotometer uses combustive gases as previously described, a variety of measures for safety are conventionally taken. For example, in the apparatus described in Patent Document 1, the gas supply pressure is always monitored, and in the case where the pressure of the gas decreases while a flame is burning, the supply of the gas is automatically halted in order to safely extinguish the flame. As described earlier, a decrease in the pressure of gas supply is one of the causes of the flashback. Therefore, detecting a decrease in the pressure of gas supply and extinguishing the flame can prevent a flashback.

In the apparatuses described in Patent Documents 2 and 3, and other documents, in order to prevent the fuel gas from leaking after the flame goes out, the intensity of light of the flame is always monitored while burning. When the intensity of light falls below the value of normal burning, the flame is automatically extinguished and the supply of the fuel gas is halted. Such a safety mechanism is employed in actual apparatuses to ensure their safety, as in Atomic Absorption Spectrophotometer AA6300, the details of which are disclosed on Shimadzu Corporation's website.

In practice, even with such safety measures as previously described, it is difficult to completely prevent a flashback, and a flashback could still occur with a very low probability. Since, in a conventional flame atomic absorption spectrophotometer, the flame goes out when a flashback occurs, the safety mechanism as previously described halts the supply of the fuel gas and the supporting gas. Thus, the gases are prevented from leaking If, after the gas supply to the burner is halted and the flame is extinguished in this manner, the operator performs an ignition operation again by pressing the ignition button, the fuel gas and supporting gas is supplied to the burner again and the flame is created in accordance with a predetermined ignition sequence. That is, in a conventional flame atomic absorption spectrophotometer, even after a flashback occurs and the flame is once extinguished, the apparatus can be resumed in use.

However, in the event of a flashback, albeit depending on the scale of the explosion, the burner head may fall apart from the chamber or the burner head may be damaged by the energy of the explosion. In some cases, the chamber itself or the gas supply pipes might be broken. If, on the other hand, the burner head, chamber, gas supply pipe, or other unit is broken so slightly as to be apparently unrecognizable, the operator might resume using the apparatus without knowing the damage in the apparatus, which might lead to a serious secondary damage.

If the operator of the apparatus is an engineer or an expert having a compiled knowledge of analysis, he/she often recognizes the problems that may occur in case of a flashback. Hence, the operator does not restart the apparatus immediately after the flashback, but can smoothly take an appropriate action such as reporting the event to a maintenance staff of the apparatus. However, in recent years, an increasing number of unskilled operators and persons having less knowledge have come to operate a flame atomic absorption spectrophotometer, who might restart the apparatus without a careful consideration. Under such circumstances, measures for higher safety than before are required in flame atomic absorption spectrophotometers.

Patent Document 1: Japanese Unexamined Patent Application Publication No. H11-183376
Patent Document 2: Japanese Unexamined Patent Application Publication No. H07-294424
Patent Document 3: Japanese Unexamined Patent Application Publication No. 2005-69763

SUMMARY OF THE INVENTION

The present invention has been achieved in view of the aforementioned problems, and the objective thereof is to provide a flame atomic absorption spectrophotometer having a higher safety in that, in the event of a flashback, the secondary accident accompanying the flashback is prevented without fail.

The present invention achieved to solve the aforementioned problem provides a flame atomic absorption spectrophotometer in which a combustion gas is burned by a burner to form a flame and a nebulized sample is atomized in the flame, including:

a) a flashback detector for detecting an occurrence of a flashback phenomenon of the flame or detecting a state in which a flashback phenomenon is considered to have occurred;

b) an ignition inhibitor for inhibiting, in the case where a flashback is detected by the flashback detector, an ignition after the detection; and c) an inhibition canceller for canceling, in an ignition inhibit state created by the ignition inhibitor, the ignition inhibit state only by a predetermined operation which is secret at least to normal users.

In the flame atomic absorption spectrophotometer according to the present invention, if a flashback occurs and the flame is extinguished, the ignition inhibitor inhibits ignition after that. Conventionally, a simple operation by a user, such as pressing an ignition button, allowed a re-ignition. On the other hand, in the flame atomic absorption spectrophotometer according to the present invention, a re-ignition cannot be performed by such a simple operation. Only when a predetermined operation which is secret at least to normal users is performed, the inhibition canceller cancels the ignition inhibit state, and enables a re-ignition.

The "normal users" include not only operators who perform an analysis operation at the user end in which the apparatus is used but also an administrator of the apparatus at the user end. Alternatively, the "normal users" include such operators, but exclude the administrator of the apparatus. Conversely, a person who is not a "normal user" and can know the predetermined operation is typically: a manufacturer itself of the apparatus and a service company itself which is responsible for the maintenance and repair of the apparatus; or a technical personnel belonging to them. That is, it is a person who can check the state of the apparatus after a flashback has occurred, and can appropriately determine and judge whether or not the use of the apparatus can be resumed.

The "predetermined operation which is secret" represents not an open operation which is described in an instruction manual or other documents that the aforementioned normal users can read, but a closed operation that only a technical personnel or other persons know. In the case where it is an operator that actually performs the predetermined operation, the operator needs to know the operation procedure. Therefore, strictly speaking, the operation will be no longer "secret" then. Nonetheless, if the operation procedure cannot be repeatedly used (i.e. can be used only once), the predetermined operation can be considered to be "secret."

As a specific example, the predetermined operation includes an entry of a password. That is, only a person who knows this password is able to cancel the ignition inhibit state.

In an embodiment, the flame atomic absorption spectrophotometer according to the present invention may preferably further include a flashback count memory for counting detection of a flashback by the flashback detector and storing the number of count, and the predetermined operation for canceling the ignition inhibit state is changed in accordance with the number of count stored in the flashback count memory.

As the flashback count memory, a nonvolatile memory, for example, may be used so that the number of count that has once stored can be held even after the power to the apparatus is halted.

This configuration enables an accurate understanding of how many times a flashback occurred in the past in the flame atomic absorption spectrophotometer. Therefore, when any operation is performed after a flashback occurs, the inhibition canceller can correctly determine whether or not the operation is appropriate in accordance with the number of occurrences of the flashback, preventing a cancellation of the ignition inhibit state by an erroneous or incorrect operation. Accordingly, even if a normal user is informed of the predetermined operation to be able to ignite the flame again after an occurrence of a flashback and this user performs the same operation after another occurrence of a flashback, it is assured that the ignition inhibit state will not cancelled, i.e. the apparatus cannot be used. This ensures a high safety of the apparatus.

In the case where a password is used as previously described, different passwords may be used in accordance with the number of occurrence of a flashback. In this case, the inhibition canceller may preferably include:

a verification information setting unit for setting a verification password in accordance with the number of count stored in the flashback count memory; and a password verifier for comparing a password entered from outside with the verification password, and, if they match, for canceling the ignition inhibit state.

The verification information setting unit may hold predetermined passwords in correspondence to the number of occurrences of a flashback, or may create a series of passwords according to a predetermined algorithm having reproducibility.

With this configuration, even if a person who was informed of the password for a first flashback tries to cancel the ignition inhibit state using the same password when a second flashback occurred, the ignition inhibit state cannot be cancelled. Accordingly, when a flashback has occurred for the second time or later, this configuration prevents the cancellation of the ignition inhibit state without being checked whether or not the apparatus can be resumed.

The password may be a predetermined password, or a one-time password. A one-time password is a single-use password which can be used for a single operation. When a person who is informed of a one-time password uses it once to cancel an ignition inhibit state, the password becomes invalid. Hence, in the event of a next flashback, even if the person uses a password that has been provided before, the ignition inhibit state will not be cancelled.

In the case where a password is used as just described, in order to secure the safety of the apparatus, it is important who issues the password, to whom it is provided, and under which conditions it is issued and provided. In other words, the method of managing and operating the password is important. As an example, when a flashback has occurred and the apparatus cannot be resumed, on a request of the user, a person in charge of the manufacturer or a service company checks the state of the apparatus after the flashback. If the safety of the resumption of the apparatus can be assured, the person in charge uses a password that has been provided from the manufacturer and cancels the ignition inhibit state to enable the apparatus to be used again. In principle, it is better not to provide the password to the user's side. However, in some cases (for example, in the case where a person in charge of a service company is not able to go to the user but can remotely assure the safety of the continuous use of the apparatus), the password may be provided to the user's side, allowing the user himself or herself to cancel the ignition inhibit state to enable the apparatus to be used again. Of course, the manner of managing and using a password is not limited to this example. By modifying the manner, the security can be extremely increased while posing a little cumbersome procedure to the user, or inversely, the procedure may be simplified while leaving the security under the user's responsibility. In this way, it is possible to control the balance between the assurance of safety and the cumbersomeness of the procedure of the use of the apparatus.

In general, a damage to the apparatus due to a flashback is probably dependent on the number of occurrences of a flashback. Hence, when the number of occurrences of a flashback reaches a predetermined number, the possibility of a secondary accident will be increased. Given this factor, when the number of count stored in the flashback count memory reaches a predetermined number, it is preferable not to allow the cancellation of the ignition inhibit state through the predetermined operation but to require the apparatus to be sent to the manufacturer with a request to examine or repair it if necessary. In this case, at the end of manufacturer, a necessary repair such as part replacement is performed, a person having a specific authority (or a person who has judged that the apparatus is equivalent to that when it was purchased, from the standpoint that there is no influence of flashbacks) resets the number of count stored in the flashback count memory to put the apparatus in the state where a flame can be ignited. Then, the apparatus is returned to the user.

A variety of manners can be used for the flashback detector to detect that a flashback phenomenon of a flame has occurred or detect a state in which a flashback phenomenon is considered to have occurred. For example, a sound sensor for detecting an explosion sound by a flashback; a pressure sensor, which is attached to the inside of chamber, for detecting a sudden change of pressure by an explosion; a vibration sensor for detecting a vibration by an explosion; or other type of sensor can directly detect an occurrence of a flashback.

Alternatively, an occurrence of a flashback may be indirectly detected by detecting a state in which it is empirically and highly probable that a flashback has occurred. For example, the inventor of the present invention and other researchers have studied and experimentally found that a flashback occurs in the following extremely rare condition: while a flame was burning using acetylene as a fuel gas and nitrous oxide as a supporting gas, the extinction of the flame was detected without detecting the decrease in pressure of the supply of the gases. Hence, detecting such a condition enables to detect, although indirectly, an occurrence of a flashback with high probability.

In the flame atomic absorption spectrophotometer according to the present invention, when a flashback occurs, a user cannot perform a re-ignition or other operation without carefully checking the apparatus to resume it. The apparatus cannot be resumed unless an instruction or a permission is provided from an engineer of the manufacturer or other person in charge for example. Basically, a flashback occurs very rarely. However, when a flashback ever occurs, this spectrometer can prevent a secondary accident caused by a breakage of a part or a structural deficiency generated by the flashback, ensuring a higher safety than before.

EXPLANATION OF THE NUMERALS

1 . . . Apparatus Main Body
10 . . . Burner
11 . . . Burner head
12 . . . Chamber
13 . . . Spray Unit
14 . . . Flame
15 . . . Ignition Unit
17 . . . Optical Sensor
18 . . . Gas Control Unit
MV1 . . . Air Valve
MV2 . . . $N_2O$ Valve
MV3 . . . $C_2H_2$ Inlet Valve
MV4 . . . Bypass Valve
MV5 . . . $C_2H_2$ Outlet Valve
MV6 . . . Pilot Valve
FR . . . Resistance Tube
PS1, PS2 . . . Pressure Sensor
PR1 . . . Pressure Controller
NV1 . . . Electric Needle Valve
NV2, NV3 . . . Manual Needle Valve
L1 . . . Fuel Gas Supply Path
L2 . . . Bypass Flow Path
L3 . . . Supporting Gas Supply Path
20 . . . Apparatus Controller
21 . . . Ignition/Extinction Controller
22 . . . Gas Controller
23 . . . Flashback Occurrence Detector
24 . . . Nonvolatile Memory
25 . . . Drive Unit
26 . . . Ignition Button
27 . . . Extinction Button
4 . . . Personal Computer
40 . . . Password Verification Unit
41 . . . Operation Unit
42 . . . Display Unit
5 . . . Communication Wire

DETAILED DESCRIPTION OF PREFERRED EMBODIMENT

Figure 1:
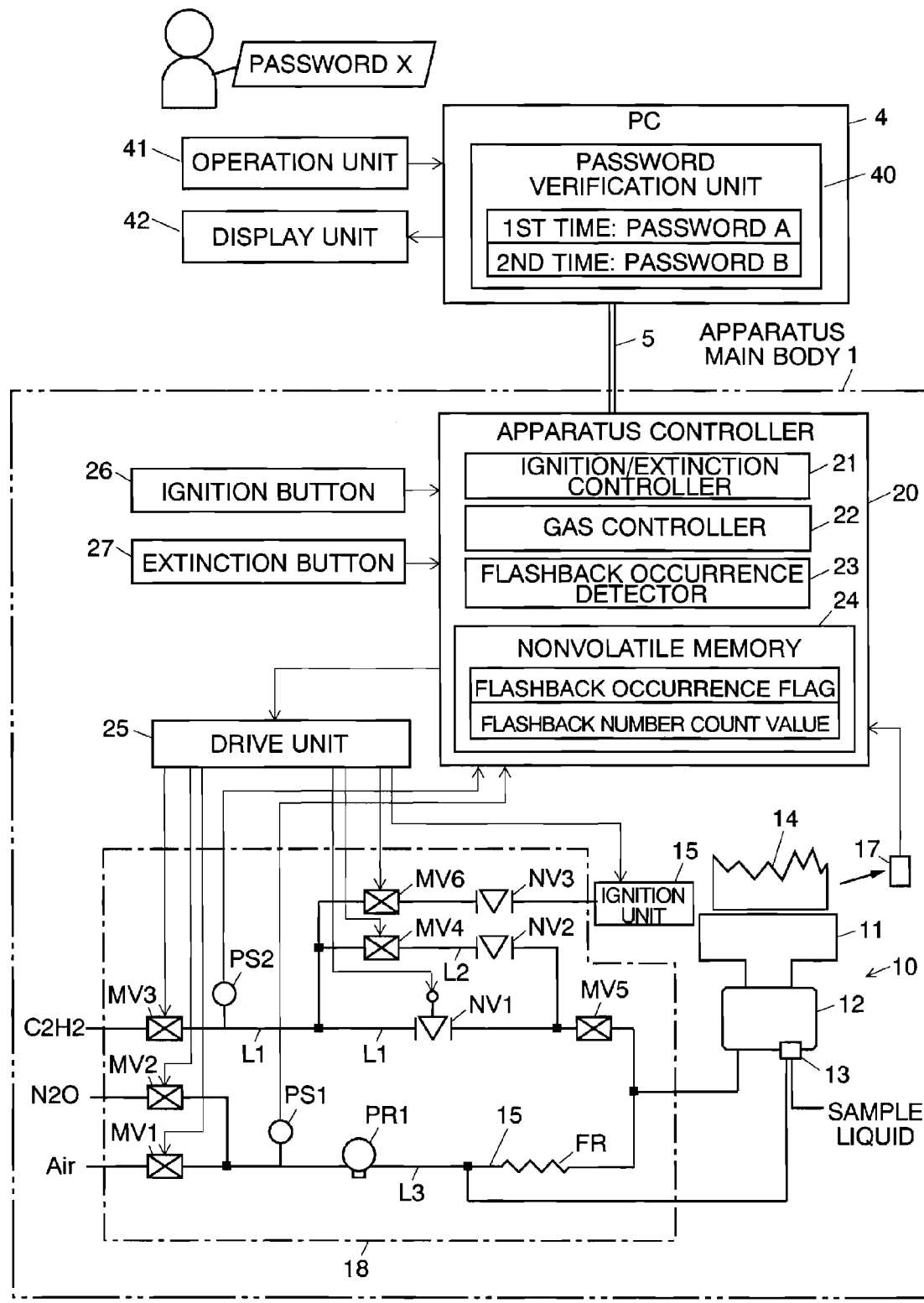
FIG. 1 is a configuration diagram of the main portion of the flame atomic absorption spectrophotometer according to an embodiment of the present invention.

Hereinafter, an embodiment of the flame atomic absorption spectrophotometer according to the present invention will be described with reference to figures. FIG. 1 is a configuration diagram of the main portion of the flame atomic absorption spectrophotometer according to the present embodiment. This flame atomic absorption spectrophotometer is composed of an apparatus main body 1 and a personal computer (PC) 4 for controlling and processing, which are connected to each other via a communication wire 5.

In the apparatus main body 1, a burner 10 includes: a spray unit 13 for nebulizing a sample liquid; a chamber 12 for mixing a fuel gas and a nebulized sample liquid; and a burner head 11 for flowing the mixed gas upward and burning it to form a flame 14. A combustion gas is supplied to the chamber 12 from a gas control unit 18. The combustion gas is a mixed gas of acetylene ($C_2H_2$) as a fuel gas and air or nitrous oxide ($N_2O$) as a supporting gas. To the burner 10 is provided an ignition unit 15 for igniting the flame. In addition, in the vicinity of the flame 14, an optical sensor 17 for detecting the light of the flame is placed in order to monitor whether or not the flame 14 exists.

In the gas control unit 18, along a fuel gas supply path L1 in which acetylene flows from a tank or other source (not shown), the following components are provided, from the upstream side: a $C_2H_2$ inlet valve MV3, a second pressure sensor PS2, an electric needle valve NV1, and a $C_2H_2$ outlet valve MV5. Along a bypass flow path L2, which is provided in parallel with the electric needle valve NV1, are provided a bypass valve MV4 and a manual needle valve NV2. Acetylene bifurcates before the inlet of the electric needle valve NV1 and flows through a pilot valve MV6 and a manual needle valve NV3 to be supplied as a pilot gas to the ignition unit 15. The degree of opening of each of the manual needle valves NV2 and NV3 is so adjusted in advance that the gas flow rate is appropriate.

Nitrous oxide and air, both of which are supplied from a tank or other source (not shown), respectively pass through an $N_2O$ valve MV2 and an air valve MV1, and converge together to be sent to a supporting gas supply path L3. Along the supporting gas supply path L3, the following components are provided, from the upstream side: a first pressure sensor PS1, a pressure controller PR1, and a resistance tube FR. The fuel gas supply path L1 and the supporting gas supply path L3 converge at a downstream of the resistance tube FR and on the outlet side of the $C_2H_2$ outlet valve MV5, respectively, to be connected to the chamber 12. The supporting gas bifurcates at an upstream of the resistance tube FR so that a portion of the supporting gas is supplied to the spray unit 13 as a nebulizer gas for spraying the sample liquid.

The air valve MV1, $N_2O$ valve MV2, $C_2H_2$ inlet valve MV3, bypass valve MV4, $C_2H_2$ outlet valve MV5, and pilot valve MV6 are electromagnetic valves. As with the electric needle valve NV1, their opening/closing operation and the degree of opening are controlled by a drive signal supplied from the drive unit 25 based on a control signal sent from an apparatus controller 20. An ignition operation of the ignition unit 15 is also controlled by a drive signal supplied from the drive unit 25. Gas pressure detection signals by the first and second pressure sensors PS1 and PS2, and a detection signal by the optical sensor 17 are provided as a feedback to the apparatus controller 20.

The apparatus controller 20 is mainly configured by a microcomputer including a central processing unit (CPU), a read only memory (ROM), a random access memory (RAM), and other units. To the apparatus controller 20 are connected an ignition button 26 and an extinction button 27, both of which are controlled by a user. The apparatus controller 20 includes, as a main function block, an ignition/extinction controller 21, a gas controller 22, a flashback occurrence detector 23, and other units. In addition, it includes a non-volatile memory 24 such as an electrically erasable and programmable read only memory (EEPROM) for holding a value of a flashback occurrence flag and a flashback count value. The ignition/extinction controller 21, gas controller 22, and flashback occurrence detector 23 are a function realized by executing a predetermined program stored in the ROM.

A personal computer 4 is connected to the apparatus controller 20 so that they can communicate with each other. To the personal computer 4 is connected an operation unit 41 such as a keyboard and a mouse and a display unit 42 as a standard interface. In the personal computer 4, dedicated software for integrally controlling the apparatus main body 1 and processing data obtained in the apparatus main body 1 is installed. Executing this software on the CPU in the personal computer 4 enables an operation of analysis by the apparatus main body 1, including characteristic functions which will be described later. Specifically, in the flame atomic absorption spectrophotometer according to the present embodiment, one of the function blocks realized by executing the dedicated software is a password verification unit 40.

The apparatus main body 1 also includes a light source, a spectroscope, a detector, and other units, which are not illustrated, for measuring the absorbance of the sample atomized in the flame 14.

Figure 2:
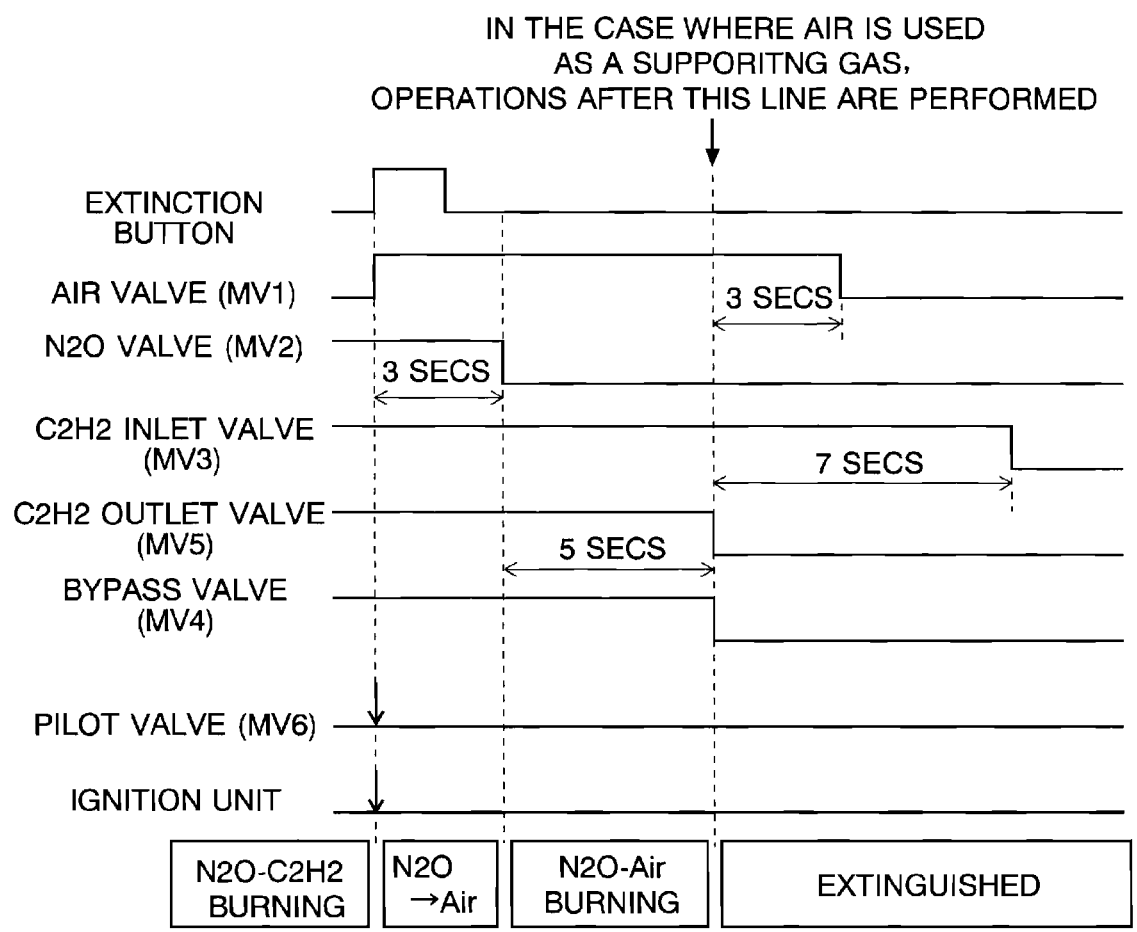
FIG. 2 is a time diagram illustrating an example of the extinction sequence in the flame atomic absorption spectrophotometer according to the present embodiment.

Before explaining characteristic operations in the flame atomic absorption spectrophotometer of the present embodiment, an extinction sequence in which a burning flame is extinguished will be simply described using the time diagram of FIG. 2. In the example of FIG. 2, a user presses the extinction button 27. The same sequence takes place also in the case where a safety mechanism is activated and an execution request for the extinction sequence is provided. In addition, nitrous oxide is used as a supporting gas in the example of FIG. 2. In the case where air is used as a supporting gas, operations after the point indicated by the downward arrow in FIG. 2 are performed.

When the extinction button 27 is pressed, the apparatus controller 20 first opens the air valve MV1 by way of the drive unit 25, and after three seconds, closes the $N_2O$ valve MV2. While both the air valve MV1 and the $N_2O$ valve MV2 are open, both air and nitrous oxide are temporarily used as a supporting gas. When the $N_2O$ valve MV2 is closed, the mixed gas of acetylene and air becomes a combustion gas. The combustion of this mixed gas forms the flame 14. Five seconds after the closure of the $N_2O$ valve MV2, both the $C_2H_2$ outlet valve MV5 and the bypass valve MV4 are closed. This halts the supply of acetylene to the chamber 12. Three seconds after the closure of the $C_2H_2$ outlet valve MV5 and the bypass valve MV4, the air valve MV 1 is closed. Furthermore, seven seconds after their closure, the $C_2H_2$ inlet valve MV3 is also closed. The closure of the air valve MV1 halts the supply of air to the chamber 12. In this manner, the flame 14 is completely extinguished.

The closing operation the air valve MV1 and the $N_2O$ valve MV2 is performed by a hardware delay circuit included in the drive unit 25 three seconds after the time point when a closing command is provided from the apparatus controller 20. Accordingly, the delays of three seconds illustrated in FIG. 2 are performed. These delays are introduced to prevent the valves from closing at the same time when an instantaneous blackout occurs, thereby a flashback is avoided at an instantaneous blackout.

Figure 3:
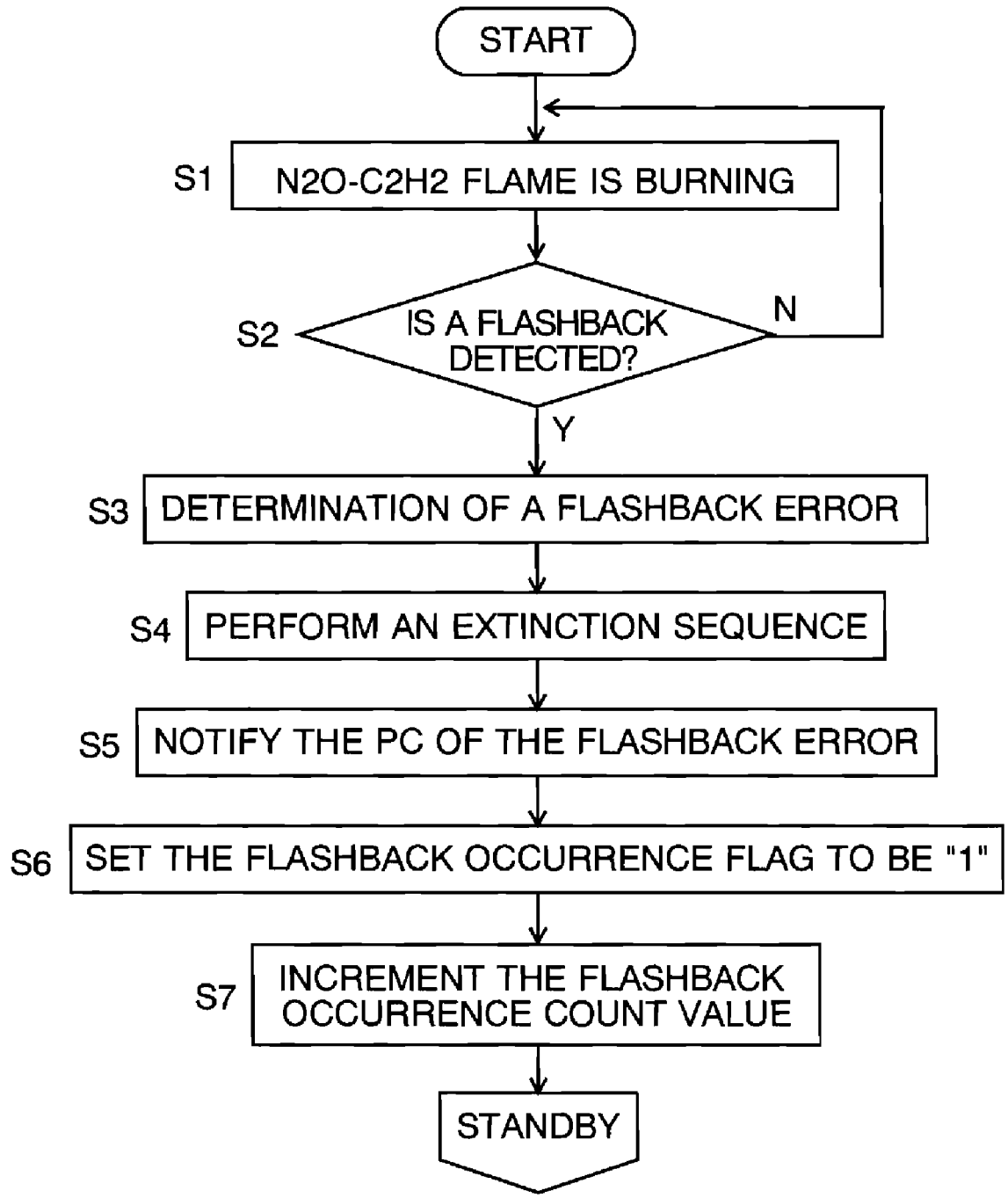
FIG. 3 is a flowchart of an operation when a flashback occurs in the flame atomic absorption spectrophotometer according to the present embodiment.
Figure 4:
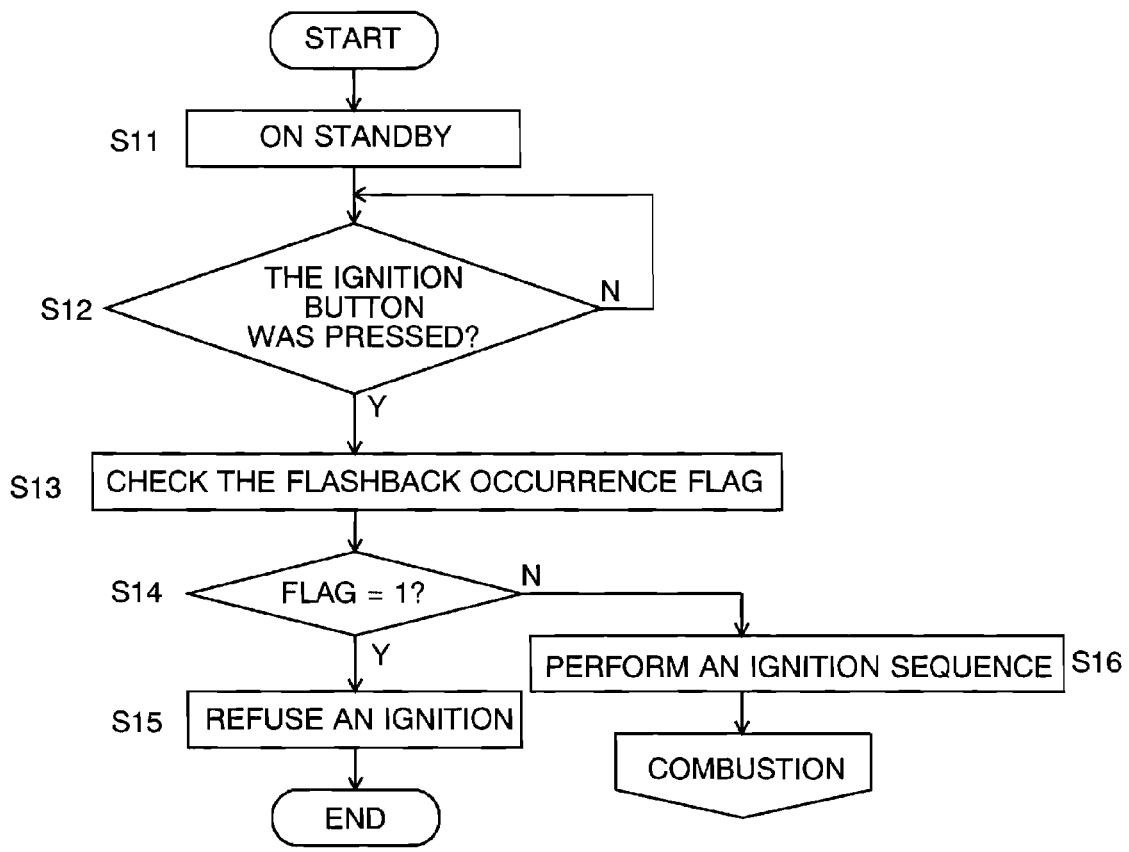
FIG. 4 is a flowchart of an operation of inhibiting ignition after a flashback has occurred in the flame atomic absorption spectrophotometer according to the present embodiment.
Figure 5:
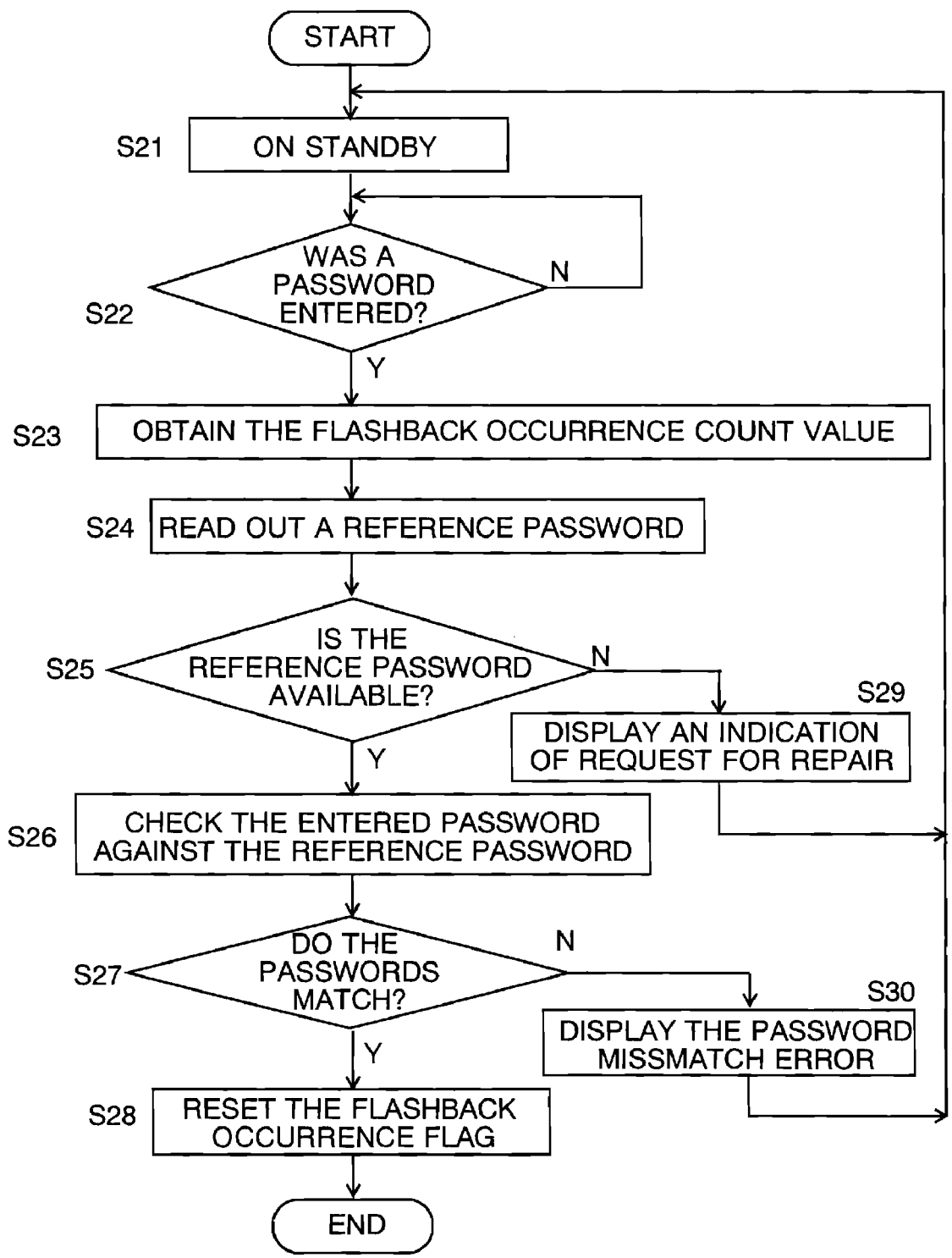
FIG. 5 is a flowchart of an operation of canceling an ignition inhibit state in the flame atomic absorption spectrophotometer according to the present embodiment.

Next, operations of inhibiting and allowing an ignition when a flashback has occurred, which is a characteristic operation in the flame atomic absorption spectrophotometer of the present invention, will be described with reference to the flowcharts of FIGS. 3 through 5. FIG. 3 is a flowchart of an operation when a flashback occurs in the flame atomic absorption spectrophotometer according to the present embodiment, FIG. 4 is a flowchart of an operation of inhibiting ignition after a flashback has occurred, and FIG. 5 is a flowchart of an operation of canceling an ignition inhibit state.

In the apparatus controller 20, when the gas pressure detected by the pressure sensor PS1 or PS2 has fallen below a predetermined threshold, the ignition/extinction controller 21 provides a direction to extinguish the flame in accordance with the extinction sequence as previously described. Also in the case where it is determined that the flame 14 has been extinguished based on the detection signal by the optical sensor 17, the ignition/extinction controller 21 gives a direction to extinguish the flame in accordance with the previously described extinction sequence. Such safety measures prevent an occurrence of a flashback, a gas leakage when the flame goes off, and other undesirable events. However, it is known that a flashback occurs in the case where a portion of the fuel gas supply path L1 near the chamber 12 is suddenly broken, or in other cases, under specific conditions.

Experiments proved that these specific conditions are the following:

(1) while a flame is burning using nitrous oxide as a supporting gas, (2) before a decrease in pressure of gas of the supporting gas or combustion gas is
   detected by the pressure sensor PS1 or PS2, and
   (3) the flame goes off while the mixture ratio of acetylene and nitrous oxide remains to be approximately the theoretical mixture ratio.

Whether or not the condition (1) is satisfied can be known by the kind of the supporting gas set as an analysis condition. Whether or not the conditions (2) and (3) are satisfied can be respectively known from the decrease in the pressure detected by the pressure sensor PS1 or PS2, and the timing of the detection that the flame has gone off based on a detection signal of the optical sensor 17. Accordingly, when the aforementioned conditions are satisfied, the flashback occurrence detector 23 in the apparatus controller 20 determines that a flashback has occurred.

Now suppose that a user sets analysis conditions, such as a selection of nitrous oxide as a supporting gas, through the operation unit 41. As a result, a command for setting a hot flame ($C_2H_2+N_2O$) as the kind of flame is sent from the personal computer 4 to the apparatus controller 20. Then, when an operation of the ignition button 26 by the user is detected, the ignition/extinction controller 21 provides a direction to perform an ignition in accordance with a predetermined hot flame ignition sequence. Based on this direction, the gas controller 22 controls the gas control unit 18 to supply acetylene and nitrous oxide to the chamber 12, and the ignition unit 15 performs an ignition operation. Consequently, the flame 14 is formed.

As illustrated in FIG. 3, while the hot flame is burning (Step S1), the flashback occurrence detector 23 monitors whether or not a flashback has occurred (Step S2). In particular, in the case where the optical sensor 17 has detected that the flame had gone off under the state that a decrease in gas pressure is not detected by neither the pressure sensor PS1 nor PS2, the flashback occurrence detector 23 determines that a "flashback error" occurred considering that a flashback took place (Step S3). As long as an occurrence of a flashback is not detected, the burning of the hot flame is continued.

In the case where a flashback error has occurred, the ignition/extinction controller 21 performs an extinction sequence as previously described to halt the supply of gases (Step S4). The flashback occurrence detector 23 notifies the personal computer 4 of the "flashback error" (Step S5). Furthermore, the flashback occurrence detector 23 sets the value of the flashback occurrence flag to be "1," increments the flashback count value, and rewrites these parameters stored in the nonvolatile memory 24 (Steps S6 and S7). While the apparatus is in a usable state, the flashback occurrence flag is "0." The flashback count value is "0" when the apparatus is purchased and when it is returned after repaired by the manufacturer as will be described later. The personal computer 4 can read out these values stored in the nonvolatile memory 24 at any time. When the extinction sequence is performed and the flame 14 is extinguished, the apparatus controller 20 returns to an idle state (or standby state).

As illustrated in FIG. 4, when the apparatus controller 20 is in the idle state (Step S11), the ignition/extinction controller 21 repeatedly determines whether or not the ignition button 26 has been pressed (Step S12). When the ignition button 26 is pressed, the ignition/extinction controller 21 reads out the flashback occurrence flag stored in the nonvolatile memory 24 (Step S13), and checks whether or not the value of this flag is "1" (Step S14). If the flag is not "1" (so that is "0"), a predetermined ignition sequence will be performed (Step S16).

In the case where a flashback is detected and the flame is extinguished, the flashback occurrence flag is set to be "1," as described earlier. In this case, the condition in Step S14 is determined to be "Y," and the ignition/extinction controller 21 refuses an ignition (Step S15). That is, the apparatus is in the ignition inhibit state. Since the flashback occurrence flag is stored in the nonvolatile memory 24, even if the power to the apparatus is turned off once and it is turned on again, the ignition inhibit state is not cancelled. Accordingly, once a flashback occurs, the apparatus cannot be resumed without taking necessary procedures.

In order to reset the flashback occurrence flag, it is necessary to enter a predetermined password through the operation unit 41 at the personal computer 4. Basically, only the manufacturer of the apparatus knows this password. That is, when the apparatus cannot be used due to an occurrence of a flashback as previously described, a user notifies the manufacturer of the fact that a flashback has occurred, directly or through a service company or the like. In the manufacturer, a technical personnel studies the generation status of the flashback and other factors. After it is confirmed that there will be no safety hazard even if the apparatus is resumed, a password for resetting the flashback occurrence flag is issued. When the number of occurred flashbacks is one, a password A is issued. This password is notified to a person in charge of the service company for example, and this person in charge goes to the user's end to enter the password through the operation unit 41.

The password may be issued in accordance with a rule that has been determined by the manufacturer, for example. Generally speaking, a manufacturer can previously estimate the degree of the damage of apparatus due to a flashback, in correspondence to the number of occurrences of flashback. Hence, in this embodiment, a password can be issued up to the second occurrence of a flashback, depending on the situation (or it is possible to determine that there is no safety hazard). For the third or later occurrence of a flashback, in order to ensure the safety, the manufacturer must take back the apparatus once to perform an examination, repair, part replacement, and other operations. Accordingly, in the manufacturer, passwords for the first and second occurrence of a flashback are respectively determined to be A and B. No password is determined for the third occurrence of a flashback.

Complying with the rule as just described, the manufacturer previously enters the passwords A and B, for the first and second occurrence of a flashback respectively, in the password verification unit 40 which is realized by dedicated software installed in the personal computer 4. As illustrated in FIG. 5, while the apparatus main body 1 including the apparatus controller 20 is in a standby state (Step S21) and a password is entered through the operation unit 41 ("Y" in Step S22), the password verification unit 40 in the personal computer 4 inquires the flashback count value of the apparatus controller 20 to obtain the value (Step S23). The password verification unit 40 internally selects a password as a reference password corresponding to the count value (Step S24). Accordingly, if the obtained flashback count value is "1," the password A becomes the reference password. If the flashback count value is "2," the password B becomes the reference password.

On the other hand, when the obtained flashback count value is "3," the password verification unit 40 cannot set the reference password. Hence, it determines whether or not the reference password is available (Step S25). If not, it displays an indication of request for repair on the display unit 42 (Step S29). If the reference password is available, the password verification unit 40 checks the entered password against the reference password (Step S26) to determine whether or not these passwords match (Step S27). If these passwords match, the personal computer 4 provides an indication to reset the flashback occurrence flag to the apparatus controller 20. In response to this indication, the apparatus controller 20 resets the flashback occurrence flag to be "0" (Step S28). That is, the ignition inhibit state is cancelled. So, after this, if the user presses the ignition button 26, the ignition/extinction controller 21 performs an ignition sequence after confirming that the flashback occurrence flag is "0." Consequently, the apparatus is enabled to be used. This corresponds to the operations of Step S12 through S14, and S16 in FIG. 4.

If a person in charge of the service company or the user enters a password (which is not a password notified from the manufacturer) on his/her own, since the entered password do not match the reference password, the process proceeds from Step S27 to Step S30, in which a massage indicating a password mismatch error is displayed on the display unit 42.

After a flashback has occurred for the second time, as in the aforementioned manner, the ignition inhibit state can be cancelled by entering the password B, which was issued by the manufacturer and is different from the password A for the first occurrence of a flashback, from the operation unit 41. Accordingly, the apparatus can be used again.

When a flashback occurs for the third time, then the flashback count value becomes "3." Since no corresponding password is prepared in the password verification unit 40 as previously described, the ignition inhibit state will not be cancelled whatever password is entered. That is, in this state, the only way to cancel the ignition inhibit state is to once send the apparatus to the manufacturer.

At the manufacturer, receiving the apparatus, a technical personnel appropriately examines and repairs it to ensure the safety of parts which may be affected by a flashback to the same extent as that assured when the apparatus was first purchased. Subsequently, the content of the nonvolatile memory 24 in the apparatus controller 20 is reset, i.e. both the flashback occurrence flag and the flashback count value are reset, and the apparatus is returned to the user. That is, the apparatus once returned to the manufacturer will be the same state as a newly-shipped apparatus at least in terms of the measures for safety against flashback. Different sets of passwords A and B may be used for each apparatus. However, since this requires a cumbersome management of passwords for each apparatus at the manufacturer, a common set of passwords A and B can be used for each apparatus to simplify the password management. If a higher security is required more than a cumbersome password management, different passwords may be used for every apparatus and the passwords may be renewed every time an apparatus is returned for a repair to the manufacturer. If passwords are changed in this manner, the operation for canceling the ignition inhibit state after the safety of the apparatus is confirmed can be left to the user.

As previously described, in the flame atomic absorption spectrophotometer according to the present embodiment, if a flashback ever occurs, the resumption of the apparatus by an easy determination of a user can be prevented. In addition, if a flashback has occurred for a predetermined number of times, the apparatus is returned to the manufacturer without fail, so that an examination and a possible repair which are inevitable for safety can be performed. Thereby, higher safety than before is ensured.

It should be noted that the embodiment described thus far is merely an example, and it is evident that any modification or adjustment can be made within the sprit of the present invention. For example, it goes without saying that the manner of managing and using a password for canceling the ignition inhibit state is not limited to what is described in the embodiment. Furthermore, the manner of detecting an occurrence of a flashback is not limited to what is described in the embodiment.

What is claimed is:

1. A flame atomic absorption spectrophotometer in which a combustion gas is burned by a burner to form a flame and a nebulized sample is atomized in the flame, comprising:
   a) a flashback detector for detecting an occurrence of a flashback phenomenon of the flame or detecting a state in which a flashback phenomenon is considered to have occurred;
   b) a flashback count memory for counting detection of a flashback by the flashback detector and storing a number of count;
   c) an ignition inhibitor for inhibiting, in a case where a flashback is detected by the flashback detector, an ignition after the detection; and
   d) an inhibition canceller for canceling, in an ignition inhibit state created by the ignition inhibitor, the ignition inhibit state only by a predetermined operation which is changed in accordance with the number of count stored in the flashback count memory.

2. The flame atomic absorption spectrophotometer according to claim 1, wherein the predetermined operation includes an entry of a password.

3. The flame atomic absorption spectrophotometer according to claim 2, wherein the inhibition canceller includes:
   a verification information setting unit for setting a verification password in accordance with the number of count stored in the flashback count memory; and
   a password verifier for comparing a password entered from outside with the verification password, and, if they match, for canceling the ignition inhibit state.

* * * * *